United States Patent [19]

Lecolier et al.

[11] Patent Number: 5,110,961

[45] Date of Patent: May 5, 1992

[54] CATALYTIC PROCESS FOR THE SYNTHESIS OF AN ALCOHOL, NEW METAL COMPLEXES AND PROCESS FOR THE SYNTHESIS OF THESE COMPLEXES

[75] Inventors: Serge Lecolier, Janville sur Juine; André Mortreux, Hem; Francis Petit, Villeneuve d'Asq; Henri Samain, Bievres, all of France

[73] Assignee: Societe Nationale des Poudres et Explosifs, Paris Cedex, France

[21] Appl. No.: 628,389

[22] Filed: Dec. 14, 1990

[30] Foreign Application Priority Data

Dec. 21, 1989 [FR] France ............... 89 16951

[51] Int. Cl.$^5$ ............ C07F 7/22; C07F 7/24; C07F 3/08; C07F 15/06
[52] U.S. Cl. .................. 556/31; 556/81; 556/118; 556/138; 568/700; 568/704; 568/716; 568/906; 568/955; 204/59 QM; 204/59 L; 205/234
[58] Field of Search ........ 556/28, 31, 81, 118, 556/138; 568/700, 704, 706, 715, 716, 906, 953; 204/58.5, 59 QM, 59 L

[56] References Cited

U.S. PATENT DOCUMENTS

| | | | |
|---|---|---|---|
| 4,254,017 | 3/1981 | Dworkin et al. | 556/81 X |
| 4,349,522 | 9/1982 | Shore et al. | 556/31 X |
| 4,360,475 | 11/1982 | Pruett et al. | 556/31 X |
| 4,404,408 | 9/1983 | Wirth et al. | 556/31 X |
| 4,551,543 | 11/1985 | Doyle et al. | 568/906 X |

Primary Examiner—Arthur C. Prescott
Attorney, Agent, or Firm—Bucknam and Archer

[57] ABSTRACT

The invention relates to a catalytic process for the synthesis of an alcohol by reaction of an epoxide with a nucleophilic compound containing a labile hydrogen, such as an alcohol, a phenol, a primary amine or a carboxylic acid.

The catalyst is a metal complex of general formula (I)

$[M[Co(CO)_4]_2]_x$ in which x is equal to 1 or 2 and M denotes tin, lead and cadmium.

The reaction preferably takes place in the presence of carbon monoxide.

This process makes it possible to increase the yield and the selectivity of the reaction and the stereoselectivity for alcohol in the case of which the hydroxyl formed is attached to the least hindered carbon atom of the epoxide.

The invention also relates to the new complexes of formula (I) in which x equals 2.

It also relates to a process for the electrosynthesis of these new compounds by electroreduction of $Co_2(CO)_8$ in an organic solvent medium in a cell in which the anode consists of the metal M, followed by isolation of the complex, the temperature of the reaction mixture and that at which the complex is isolated being lower than 25° C.

16 Claims, No Drawings

CATALYTIC PROCESS FOR THE SYNTHESIS OF AN ALCOHOL, NEW METAL COMPLEXES AND PROCESS FOR THE SYNTHESIS OF THESE COMPLEXES

The present invention relates to a catalytic process for the synthesis of an alcohol by reaction of an epoxide with a nucleophilic compound containing a labile hydrogen, such as, for example, an alcohol, a phenol, a primary amine or a carboxylic acid.

The present invention also relates to new metal complexes employed as catalysts in the abovementioned process and to a process for the synthesis of these new complexes.

The alcohols obtained according to the process of the present invention are useful especially as synthesis intermediates, particularly as intermediates for the synthesis of plant-protection derivatives.

It is known to react, in the presence of a metal complex as a catalyst, an epoxide with a nucleophilic compound containing a labile hydrogen:

$$\underset{O}{\overset{R}{\diagdown\!\!\diagup}} \xrightarrow[\text{catalyst}]{ZH} \underset{OH}{\overset{R}{\diagdown\!\!\diagup}}\!\!Z + \underset{Z}{\overset{R}{\diagdown\!\!\diagup}}\!\!OH$$

$$(1) \qquad\qquad (2)$$

with R denoting an organic radical and ZH a nucleophilic compound containing a labile hydrogen.

A mixture of the 2 alcohols (1) and (2) is thus generally obtained, together with various by-products, sometimes predominant, of epoxide isomerisation and/or polymerisation.

The major problem which arises when it is desired to obtain either the alcohol (1) or the alcohol (2) according to the abovementioned reaction is therefore twofold. It concerns, on the one hand, the selectivity for the opening of the epoxide ring as distinct from its isomerisation to a carbonyl derivative and/or its polymerisation and, on the other hand, the stereoselectivity of the opening itself, which determines the ratio of the alcohols (1) and (2).

In Tetrahedron Letters, Vol. 26, No. 27, pp. 3219-3222, 1985, Otera describes, for example, such a reaction in a neutral medium in the case of which ZH is an alcohol and the catalyst a tin-phosphate condensate.

The yields of alcohols (1)+(2) are between 57 and 86%. The alcohol (1) is very clearly predominant, and it is frequently the only alcohol obtained. This alcohol (1) corresponds to an attack of the nucleophilic moiety Z on the least hindered carbon of the epoxide.

Houben Weyl, 4th edition, Vol. 6/1a, pages 373-385, also mentions such a reaction in which ZH is an alcohol and the catalyst is tin chloride. The alcohol (1) is also obtained predominantly. The alcohol (2) is sometimes obtained predominantly only in an acidic medium, and this is a restriction on the use of the process and the recovery of the products. Now, for many applications, especially those in plant protection, it is the alcohol (2) that a person skilled in the art is seeking.

The present invention solves a twofold problem. It makes it possible to obtain the alcohol (2) predominantly or exclusively as distinct from the alcohol (1) in a neutral medium, and this is particularly advantageous when one of the reactants carries acid-sensitive groups. It also makes it possible to increase the yield and the selectivity for alcohols (1) and (2) as distinct from the epoxide polymerisation and/or isomerisation reactions.

So far as the Applicant is aware, it has never hitherto been possible to obtain a stereoselectivity close to 100% for alcohol (2), even in an acidic medium. Such a result offers especially the enormous advantage of eliminating the tricky and costly stage of separation of the alcohols (1) and (2).

The process for the synthesis of an alcohol by reaction of an epoxide with a nucleophilic compound containing a labile hydrogen in the presence of a metal catalyst according to the invention is characterised in that the catalyst is a metal complex of general formula (I)

$$[M[Co(CO)_4]_2]_x$$

in which x is equal to 1 or 2 and M denotes a metal chosen from the group consisting of tin, lead and cadium.

M preferably denotes tin.

The metal complexes of general formula (I) in which $x=1$ are known:

Hieber, in Z. Anorg. Allgem. Chem. 249 (43), 1942, describes the synthesis of $Sn[Co(CO)_4]_2$ and $Cd[Co(CO)_4]_2$ by reaction of $CoBr_2$ with the corresponding metal in the presence of carbon monoxide. No application of these compounds is described.

Magomedov, in Coordinn. Chimia 6 (5) 1980 page 770, describes the synthesis of $Sn[Co(CO)_4]_2$ according to the reaction:

$$SnCl_2 + 2NaCo(CO)_4 \xrightarrow[\text{Argon}]{\text{THF}} 2NaCl + Sn[Co(CO)_4]_2.$$

The yield is 15%. $NaCo(CO)_4$ is obtained by reaction of $Co_2(CO)_8$ with a sodium amalgam. $Sn[Co(CO)_4]_2$ is employed as a catalyst for olefin hydrosilylation.

The metal complexes of general formula (I) in which $x=2$ are new, and these new metal complexes are a further subject of the present invention.

The process for the synthesis of an above-mentioned alcohol according to the invention is generally carried out in the absence of air, in an oxygen-free atmosphere, for example under nitrogen or under argon.

The reaction preferably takes place in the presence of carbon monoxide, optionally in the presence of an inert gas such as nitrogen or argon.

In a very particularly preferred manner the carbon monoxide pressure, a partial pressure in the case of a mixture with an inert gas, is between $10^5$ and $10^7$ Pa (1 and 100 bars), preferably between $3\times10^6$ and $5\times10^6$ Pa (30 and 50 bars).

A steel reactor is perfectly suitable for carrying out the reaction according to the invention According to a preferred alternative form of the invention:

the alcohol corresponds to the general formula $$\underset{R_2\quad Z\quad R_4}{\overset{R_1\quad OH\quad R_3}{\diagdown\mid\diagup}}\!\!\underset{}{C\!-\!C} \qquad (A)$$

in which

R₁, R₂, R₃ and R₄, which are identical or different, denote:

hydrogen a saturated or unsaturated aliphatic group, preferably an alkyl or alkoxyalkyl chain containing 1 to 12 carbon atoms, unsubstituted or substituted. As examples of such aliphatic groups there may be mentioned methyl, ethyl, propyl, butyl, methoxymethyl and butoxymethyl groups and the chains

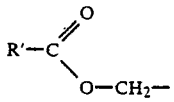

in which R, denotes an alkyl group containing 1 to 8 carbon atoms.

As examples of substituents carried by the aliphatic group there may be mentioned alkyl and alkoxyalkyl chains containing 1 to 8 carbon atoms and aromatic groups such as phenyl and naphthyl groups.

an aromatic group, preferably phenyl or naphthyl, unsubstituted or substituted, containing 1 to 18 carbon atoms. Examples of substituents which may be mentioned are especially alkyl and alkoxyalkyl chains containing 1 to 4 carbon atoms.

or else R₁ and R₂, or R₁ and R₃, form, together with the carbon atoms to which they are bonded, an aliphatic ring containing 4 to 18 carbon atoms, unsubstituted or substituted, for example by at least one alkyl chain containing 1 to 4 carbon atoms.

Examples of such rings which may be mentioned are especially cyclohexyl and cyclododecyl rings.

Z denotes a monosubstituted amino, alkoxy, aryloxy or carboxyl group.

in that the epoxide corresponds to the general formula (E)

in which R₁, R₂, R₃ and R₄ have the abovementioned meaning, and in that the nucleophilic compound containing a labile hydrogen corresponds to the general formula ZH, Z having the abovementioned meaning.

Within the scope of the present invention the epoxide of general formula (E) may be a polyepoxide. This is the case when at least one of the groups R₁, R₂, R₃ and R₄ carries an epoxide functional group.

Z is preferably an RO—, RNH— or

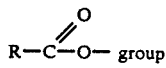

in which R denotes:

an aliphatic or cycloaliphatic group containing 1 to 48 carbon atoms, preferably a saturated or unsaturated alkyl, cycloalkyl or alkoxyalkyl group, unsubstituted or substituted preferably by at least one group G chosen from the class consisting of alkyl, alkoxy and alkoxyalkyl groups containing 1 to 18 carbon atoms, optionally substituted aromatic groups containing 1 to 18 carbon atoms and by hydroxyl, carboxyl and amino groups.

an aromatic group, preferably phenyl or naphthyl, containing 1 to 48 carbon atoms, unsubstituted or substituted preferably by at least one abovementioned group G.

Examples of such groups R which may be mentioned are methyl, ethyl, propyl, isopropyl, butyl, pentyl, hexyl, octyl, nonyl, decyl, dodecyl, phenyl, tolyl, naphthyl and 2-hydroxyphenyl groups.

In a particularly preferred manner

R₁, R₂, R₃ and R₄, which are identical or different, denote hydrogen, an alkyl or alkoxyalkyl chain containing 1 to 4 carbon atoms, or else R₁ and R₃ form, together with the carbon atoms to which they are bonded, an aliphatic ring containing 5 to 12 carbon atoms, preferably a cyclohexyl ring.

ZH denotes a monoalcohol, a polyol, a phenol, a hydroxyphenol, a primary monoamine or polyamine or a carboxylic monoacid or polyacid.

According to a preferred alternative form of the invention the alcohol of general formula (A) is synthesised even when the steric hindrance of the carbon atom carrying R₁ and R₂ of the epoxide of general formula (E) is greater than the steric hindrance of the carbon atom carrying R₃ and R₄.

This is generally the case when the total number of carbon atoms of R₁ and R₂ is greater than the total number of carbon atoms of R₃ and R₄. According to an alternative form, R₃ denotes hydrogen and R₄ denotes hydrogen or a methyl group.

The process for the synthesis of an alcohol according to the present invention can be carried out without any solvent or in an organic solvent medium. In the latter case the solvents employed are, for example, tetrahydrofuran (THF), ketones, dimethylformamide (DMF), N-methylpyrrolidone (NMP), cyclohexane, decalin, propyl carbonate and preferably aromatic solvents, especially toluene.

The concentration of the reactants in the solvent is generally between 2% and 10% by weight.

The reaction temperature is generally between 0° C. and 150° C., preferably close to 90°–100° C. The reaction period generally lasts between 0.1 h and 36 h.

The molar ratio of the nucleophilic compound containing a labile hydrogen to the epoxide is generally between 1 and 10, preferably between 1.5 and 3.

The ratio of the epoxide to the metal catalyst is generally between 100 and 500, preferably close to 200.

According to another preferred alternative form of the process for the synthesis of an alcohol according to the invention, the metal complex catalyst of general formula (I) is obtained by electroreduction of Co₂(CO)₈ in an organic solvent medium, preferably acetone, in an electrolysis cell in which the anode consists of the metal M. Other organic solvents which may be employed are, for example, propylene carbonate/benzene mixtures and THF. The cathode is inert, made, for example, of platinum or stainless steel. The complex of general formula (I) is subsequently isolated, preferably by evaporation of the solvent. Other techniques such as, for example, its precipitation by adding a nonsolvent, may be employed.

The operation is generally carried out with an applied potential, in the presence of a supporting electrolyte.

The quantity of current which is involved is greater than 2 F per mole of Co₂(CO)₈, preferably close to 4 F or greater than 4 F per mole of Co₂(CO)₈.

When the temperature of the reaction mixture and that at which the complex is isolated, preferably by evaporation of the solvent, is lower than 25° C., preferably between 10° C. and 25° C., the metal complexes of formula (I) in which x=2 are obtained.

When the temperature of the reaction mixture is higher than 35° C., preferably close to the reflux temperature of the solvent, or when the temperature at which the complex is isolated, preferably by evaporation of the solvent, is higher than 35° C., preferably close to the reflux temperature of the solvent, the metallic complexes of formula (I) in which x=1 are obtained.

A further subject of the present invention is the new metal complexes of general formula (I) in which x=2 and the abovementioned process for the electrosynthesis of these new metal complexes.

The following nonlimiting examples illustrate the invention and the advantages which it provides.

EXAMPLE 1

Electrochemical Synthesis of [Sn [Co(CO)$_4$]$_2$]$_2$ 200 mg of Co$_2$(CO)$_8$, 2 mg of NBu$_4$PF$_6$ as supporting electrolyte (Bu denoting butyl) and 25 ml of acetone are introduced into an electrolysis cell comprising only one compartment. This cell comprises a thermostatic jacket. The anode is made of tin and the cathode of platinum. A cathode potential of −0.8 V relative to Ag/AgCl is applied, and a quantity of current of 225 C is then passed through, the average current being 0.7 A.

The temperature of the reaction mixture is maintained at 15°–20° C. by a circulating cold water through the termostatic jacket.

During the electroreduction of the Co$_2$(CO)$_8$ the colour changes from light brown (Co$_2$(CO)$_8$) to orangy red, a colour due to the intermediate complex Sn[Co(CO)$_4$]$_4$, and then to green. No precipitate appears.

The solution is then transferred to a Schlenk tube and the acetone is then stripped off under vacuum at 20° C. 260 mg of [Sn[Co(CO)$_4$]$_2$]$_2$ are recovered in the form of a dark green powder. The yield is 96% based on the initial Co$_2$(CO)$_8$.

This complex was identified by elemental analysis, by electron microprobe analysis and by IR and mass spectrometry. The study of the FAB (fast atom bombardment) mass spectrum obtained in a thioglycerol matrix enables, in particular, the molecular mass to be determined. A more thorough study of the spectrum, taking into consideration the various tin isotopes, is consistent with the empirical formula Sn$_2$CO$_4$(CO)$_{16}$.

EXAMPLE 2

Electrochemical Synthesis of Sn[Co(CO)$_4$]$_2$ 200 mg of Co$_2$(CO)$_8$, 2 mg of NBu$_4$PF$_6$ as supporting electrolyte and 25 ml of acetone as solvent are introduced into an electrolysis cell comprising only a single compartment. The anode is made of tin and the cathode of platinum.

The cell is maintained under an inert gas (nitrogen). A cathode potential of −0.8 V relative to Ag/AgCl is applied and 225 C are then passed through, the average current being 0.7 A. The temperature of the reaction mixture rises up to the reflux temperature of the solvent (55° C.).

The solution is then transferred to a Schlenk tube and the acetone is then stripped off under vacuum at 30°–35° C.

Sn[Co(CO)$_4$]$_2$ is recovered in the form of a violet powder.

This complex was identified using the same techniques as those employed in Example 1 and by electron paramagnetic resonance (EPR).

EXAMPLES 3 TO 8

Synthesis of Isopropoxycyclohexanol by Reaction of Epoxycyclohexane with Isopropanol Examples 3 to 7 are carried out according to the process of the present invention.

Example 8 is a comparative example performed with SnCl$_2$ as catalyst, according to the state of the art.

The general conditions relating to these Examples 3 to 8 are as follows:

The reactions are performed in a steel reactor of 100 cm$^3$ capacity under different carbon monoxide pressures and with mechanical stirring.

Isopropanol (24 cm$^3$) is in molar excess (2.65) relative to epoxycyclohexane (11.9 cm$^3$). It therefore acts both as reactant and as solvent.

The molar ratio of the epoxide to the catalyst is 200. In the case of Example 3 the catalyst is obtained according to Example 1 and in the case of Examples 4 to according to Example 2.

The reaction temperature is 90° C.

The catalyst is dissolved in isopropanol and this solution is then introduced into the reactor. Epoxycyclohexane is then added.

The reactor is then pressurised and then heated.

Example 7 according to the invention has been performed without CO, under a nitrogen pressure of 10$^5$ Pa.

Table 1, which follows, specifies for each example the carbon monoxide pressure, the reaction period, the nature of the catalyst, the overall degree of conversion (ODC) of epoxycyclohexane, the yield (Yld) of isopropoxycyclohexanol of formula

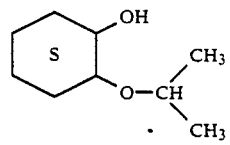

which is obtained, expressed relative to the initial epoxycyclohexane, and the corresponding selectivity (S) in respect of the epoxycyclohexane converted.

Isopropoxycyclohexanol was identified by IR, NMR and mass spectrometry.

OCD, Yld and S were obtained by gas phase chromatography and a combination of gas phase chromatography and mass spectrometry.

TABLE 1

| EX No. | Catalyst | CO pressure (in 10$^5$ Pa) | Time (in h) | ODC (%) | Yld (%) | S (%) |
|---|---|---|---|---|---|---|
| 3 | [Sn[Co(CO)$_4$]$_2$]$_2$ | 45 | 16 | 100 | 99.9 | 99.9 |
| 4 |  | 45 | 16 | 100 | 99.9 | 99.9 |
| 5 | Sn[Co(CO)$_4$]$_2$ | 45 | 2 | 100 | 99.9 | 99.9 |
| 6 |  | 1 | 16 | 100 | 99.9 | 99.9 |
| 7 |  | 0 | 16 | 61 | 56 | 92 |
| 8 | SnCl$_2$ | 45 | 16 | 36 | 24 | 66 |

EXAMPLE 9

Synthesis of 2(n-butylamino)cyclohexanol by Reaction of Epoxycyclohexane with n-butylamine A solution of 270 mg of [Sn[CO(CO)$_4$]$_2$]$_2$ obtained according to Example 1 in 10 cm$^3$ of benzene is introduced into a steel reactor 100 cm$^3$ in capacity with mechanical stirring.

11.9 cm$^3$ of epoxycclohexane and 25 ml of n-butylamine are then introduced. The reactor is pressurised with carbon monoxide (45 × 10$^5$ Pa), and is then heated to 90° C. with stirring for 16 h.

The ODC of the opoxide, the yield of 2-(n-butylamino)cyclohexanol formed, of formula

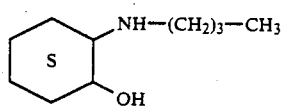

expressed relative to the initial epoxide and the corresponding selectivity in respect of the epoxycyclohexane converted, are 100%.

2-n-Butylaminocyclohexanol was identified by IR, NMR and mass spectrometry.

The ODC, the yield and the selectivity were obtained by gas phase chromatography and a combination of gas phase chromatography and mass spectrometry.

EXAMPLES 10 to 13

Synthesis of 1-phenoxy-1-hydroxymethylethane (A1) and of 1-phenoxy-2hydroxypropane (B1) by Reaction of Epoxypropane with Phenol

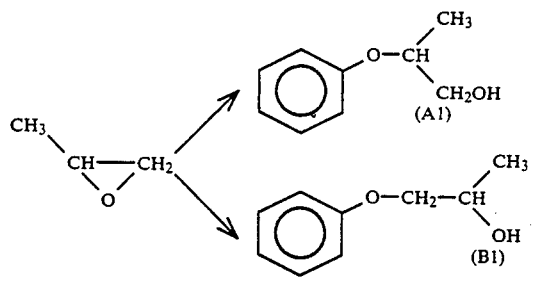

B1 corresponds to abovementioned alcohol (1) and A1 to the abovementioned alcohol (2).

Examples 10 to 12 are performed according to the process of the present invention, with the Sn[Co[CO)$_4$]$_2$ catalyst obtained according to Example 2 in the case of Examples 10 and 11, and with the [Sn[Co(-CO)$_4$]$_2$]$_2$ catalyst obtained according to Example 1 in the case of Example 12. Example 13 is a comparative example performed according to the state of the art with SnCl$_2$ as catalyst.

A solution of catalyst in 26 g of phenol, a solution which is kept liquid by gentle heating, is introduced into a steel reactor 100 cm$^3$ in capacity with mechanical stirring.

8.2 cm$^3$ of epoxypropane are then introduced.

The molar ratio of epoxypropane to the catalyst is 200.

The reactor is pressurised with carbon monoxide (45 × 10$^5$ Pa) and is then heated to 90° C. with stirring for 2.5 h in the case of Example 10, and for 16 h in the case of Examples 11 to 13.

Table 2, which follows, specifies for each example the ODC (%) of the epoxide, the yields $R_{B1}$ and $R_{A1}$ of each of the 2 alcohols B1 and A1 which are formed, expressed in % relative to the initial epoxypropane, the selectivity $S_{A1+B1}$ for alcohols A1 and B1 which are formed, in respect of the epoxide converted [$S_{A1+B1} = 100 \times (R_{A1}+R_{B1})/ODC$] and the stereoselectivity $SS_{A1}$ for the formation of the alcohol A1 as distinct from the formation of the alcohol B1 [$SS_{A1} = 100 \times R_{A1}/(R_{A1}+R_{B1})$].

The determinations of the contents of epoxide and alcohols A1 and B1 were carried out using gas phase chromatography.

The ratio of the alcohols A1 and B1 was obtained using NMR of carbon 13.

The alcohol A1, in which $R_1 = CH_3$ and $R_2 = R_3 = R_4 = H$ with reference to the general formula (A), is obtained predominantly, even though the steric hindrance of the carbon atom carrying $R_1$ and $R_2$ of the epoxide is greater than the steric hindrance of the carbon atom carrying $R_3$ and $R_4$, with reference to the general formula (E).

TABLE 2

| EX No. | ODC (%) | $S_{A1+B1}$ (%) | $R_{B1}$ (%) | $R_{A1}$ (%) | $SS_{A2}$ (%) |
|---|---|---|---|---|---|
| 10 | 92 | 100 | NOT DETERMINED | | |
| 11 | 100 | 100 | 30 | 70 | 70 |
| 12 | 100 | 100 | 30 | 70 | 70 |
| 13 | 92 | 89 | 41 | 41 | 50 |

EXAMPLES 14 TO 18

Synthesis of 2-(1,1-diemthyl-2-hydroxy-ethoxy)phenol (A2) by reaction of 2-methyl-1,2-epoxypropane (MEP) With Catechol

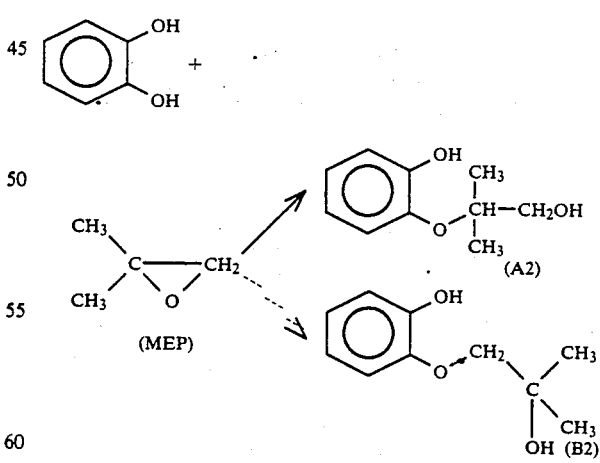

B2 corresponds to the abovementioned alcohol (1) and A2 to the abovementioned alcohol (2).

The alcohol A2 is especially advantageous as a precursor of benzofuranol, itself a precursor of carbofuran, a well-known plant-protection derivative.

Examples 14 to 17 are carried out with the [Sn[Co(-CO)$_4$]$_2$]$_2$ catalyst obtained according to Examples 1 and Example 18 with the Sn[Co(CO)$_4$]$_2$ catalyst obtained according to Example 2.

A solution of the catalyst in an organic solvent is introduced into a Schlenk tube cooled using an ice bath: 67 mg of catalyst in 20 cm$^3$ of acetone in the case of Example 4, 247 mg of catalyst in 20 cm$^3$ of THF in the case of Example 15, 117 mg of catalyst in 20 cm$^3$ of isopropanol in the case of Example 16, 67 mg of catalyst in 20 cm$^3$ of propylene carbonate in the case of Example 17 and 67 mg of catalyst in 20 cm$^3$ of propylene carbonate in the case of Example 18.

Catechol is then added (13 g, 12.9 g, 1.6 g, 2 g and 3.2 g in the case of Examples 14 to 18 respectively).

The solution is stirred for a few minutes at 0° C. and MEP is then added dropwise (10 cm$^3$ in the case of Examples 14 and 15, 1.25 cm: in the case of Example 16, 1.7 cm$^3$ in the case of Example 17 and 2.5 cm$^3$ in the case of Example 18).

The reaction takes place under nitrogen atmosphere (10$^5$ Pa), at 0° C., for 15 min in the case of Example 14, 30 min in the case of Example 15, 5 min in the case of Example 16, 10 min in the case of Example 17 and 3 h in the case of Example 18.

Identification of the products and the stereoselectivity for alcohols A2 and B2 were determined using NMR of carbon 13 and by a combination of gas phase chromatography and mass spectrometry. The alcohol A2 was determined quantitatively by gas phase chromatography.

The alcohol A2 is obtained in the following yield, expressed relative to the initial MEP:

Example 14 : 20%
Example 15 : 20%
Example 16 : 25%
Example 17 : 18%
Example 18 : 30%

No formation of the alcohol B2 is observed in any of these examples.

The stereoselectivity SS$_{A2}$ for the formation of the alcohol A2 as distinct from the formation of the alcohol B2 is therefore close to 100%.

The alcohol A2, in which R$_1$=R$_2$=CH$_3$ and R$_3$=R$_4$=H with reference to the general formula (A) is obtained exclusively, even though the steric hindrance of the carbon atom carrying R$_1$ and R$_2$ of the epoxide is greater than the steric hindrance of the carbon atom carrying R$_3$ and R$_4$, with reference to the general formula (E).

We claim:

1. Process for the synthesis of an alcohol by reaction of an epoxide with a nucleophilic compound containing a labile hydrogen in the presence of a metal catalyst, characterised in that the catalyst is a metal complex of general formula (I) [M[Co(CO)$_4$]$_2$]$_x$ in which x is equal to 1 or 2 and M denotes a metal chosen from the group consisting of tin, lead and cadmium, preferably tin.

2. Process for the synthesis of an alcohol according to claim 1, characterised in that the reaction takes place in the presence of carbon monoxide.

3. Process for the synthesis of an alcohol according to claim 2, characterised in that the carbon monoxide pressure is between 10$^5$ and 10$^7$ Pa, preferably between 3×10$^5$ and 5×10$^6$ Pa.

4. Process for the synthesis of an alcohol according to claim 1, characterised in that the alcohol corresponds to the general formula (A)

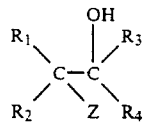

in which:

R$_1$, R$_2$, R$_3$ and R$_4$, which are identical or different, denote:
hydrogen
a saturated or unsaturated aliphatic group, preferably an alkyl chain, containing 1 to 12 carbon atoms, unsubstituted or substituted
an aromatic group, preferably phenyl or naphthyl, unsubstituted or substituted, containing 1 to 18 carbon atoms
or else R$_1$ and R$_2$ or R$_1$ and R$_3$, together with the carbon atoms to which they are bonded, form an aliphatic ring containing 4 to 18 carbon atoms, unsubstituted or substituted.

Z denotes a monosubstituted amino, alkoxy, aryloxy or carboxyl group in that the epoxide corresponds to the general formula (E)

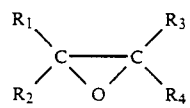

in which R$_1$, R$_2$, R$_3$ and R$_4$ have the abovementioned meaning, and in that the nucleophilic compound containing a labile hydrogen corresponds to the general formula ZH, Z having the abovementioned meaning.

5. Process for the synthesis of an alcohol according to claim 4, characterised in that the group Z is an RO—, RNH— or

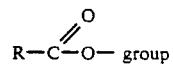

in which R denotes:

an aliphatic or cycloaliphatic group containing 1 to 48 carbon atoms, preferably an alkyl, cycloalkyl or alkoxyalkyl group, saturated or unsaturated, unsubstituted or substituted preferably by at least one group G chosen from the group consisting of alkyl, alkoxy and alkoxyalkyl groups containing 1 to 18 carbon atoms, of optionally substituted aromatic groups containing 1 to 18 carbon atoms and of hydroxyl, carboxyl and amino groups;

an aromatic group, preferably phenyl or naphthyl, containing 1 to 48 carbon atoms, unsubstituted or substituted preferably by at least one abovementioned group G.

6. Process for the synthesis of an alcohol according to claim 5, characterised in that:

R$_1$, R$_2$, R$_3$ and R$_4$, which are identical or different, denote hydrogen, an alkyl or alkoxyalkyl chain containing 1 to 4 carbon atoms, or else R$_1$ and R$_3$ form, together with the carbon atoms to which they are bonded, an aliphatic ring containing 5 to 12 carbon atoms, preferably a cyclohexyl ring;

ZH denotes a monoalcohol, a polyol, a phenol, a hydroxyphenol, a primary monoamine or polyamine or a carboxylic monoacid or polyacid.

7. Process for the synthesis of an alcohol of general formula (A) according to claim 4 characterised in that the steric hindrance of the carbon atom carrying $R_1$ and $R_2$ of the epoxide of general formula (E) is greater than the steric hindrance of the carbon atom carrying $R_3$ and $R_4$.

8. Process for the synthesis of an alcohol of general formula (A) according to claim 7, characterised in that the total number of carbon atoms of $R_1$ and $R_2$ is greater than the total number of carbon atoms of $R_3$ and $R_4$.

9. Process for the synthesis of an alcohol of general formula (A) according to claim 8, characterised in that $R_3$ denotes hydrogen and $R_4$ denotes hydrogen or a methyl group.

10. Process for the synthesis of an alcohol according to claim 1, characterised in that the molar ratio of the epoxide to the metal catalyst is between 100 and 500.

11. Process for the synthesis of an alcohol according to claim 1, characterised in that the molar ratio of the nucleophilic compound containing a labile hydrogen to the epoxide is between 1 and 10, preferably between 1.5 and 3.

12. Process for the synthesis of an alcohol according to claim 1, characterised in that the reaction temperature is between 0° C. and 150° C. and in that the reaction period lasts between 0.1 h and 36 h.

13. Process for the synthesis of an alcohol according to claim 1, characterised in that the catalyst of general formula (I) is obtained by electroreduction of $Co_2(CO)_8$ in an organic solvent medium, in an electrolysis cell in which the anode consists of the metal M.

14. Process for the synthesis of an alcohol according to claim 13, characterised in that the electroreduction of $Co_2(CO)_8$ is conducted in acetone, with applied potential, in the presence of a supporting electrolyte, involving a quantity of current greater than 2 F per mole of $Co_2(CO)_8$, preferably close to 4 F or greater than 4 F per mole of $Co_2(CO)_8$.

15. Metal complexes of general formula $[M[Co(CO)_4]_2]_2$ in which M denotes a metal chosen from the group consisting of tin, lead and cadmium.

16. Process for the electrosynthesis of a metal complex according to claim 15, characterised in that it is obtained by electroreduction of $Co_2(CO)_8$, in an organic solvent medium, in an electrolysis cell in which the anode consists of the metal M, and in that the complex is then isolated, the temperature of the reaction mixture and that at which the complex is isolated being lower than 25° C., preferably between 10 and 25° C.

* * * * *